US011182907B2

(12) United States Patent
Lachaine

(10) Patent No.: US 11,182,907 B2
(45) Date of Patent: Nov. 23, 2021

(54) MOTION MANAGEMENT IN IMAGE-GUIDED RADIOTHERAPY USING CONTOUR ELEMENTS

(71) Applicant: Elekta LTD., Montreal (CA)

(72) Inventor: Martin Emile Lachaine, Montreal (CA)

(73) Assignee: Elekta LTD., Montreal (CA)

( * ) Notice: Subject to any disclaimer, the term of this patent is extended or adjusted under 35 U.S.C. 154(b) by 0 days.

(21) Appl. No.: 16/074,632

(22) PCT Filed: Oct. 21, 2016

(86) PCT No.: PCT/IB2016/001601
§ 371 (c)(1),
(2) Date: Aug. 1, 2018

(87) PCT Pub. No.: WO2017/134482
PCT Pub. Date: Aug. 10, 2017

(65) Prior Publication Data
US 2019/0080459 A1    Mar. 14, 2019

Related U.S. Application Data

(60) Provisional application No. 62/290,198, filed on Feb. 2, 2016.

(51) Int. Cl.
*G06T 7/246* (2017.01)
*G06T 7/00* (2017.01)
(Continued)

(52) U.S. Cl.
CPC ............. *G06T 7/246* (2017.01); *A61N 5/107* (2013.01); *A61N 5/1045* (2013.01);
(Continued)

(58) Field of Classification Search
None
See application file for complete search history.

(56) References Cited

U.S. PATENT DOCUMENTS

| 2006/0002601 A1 | 1/2006 | Fu et al. |
| 2006/0074292 A1* | 4/2006 | Thomson ............... A61B 6/032 600/411 |

(Continued)

FOREIGN PATENT DOCUMENTS

| CN | 1672651 A | 9/2005 |
| CN | 101501704 A | 8/2009 |

(Continued)

OTHER PUBLICATIONS

"Australian Application Serial No. 2016391118, First Examination Report dated Feb. 22, 2019", 5 pgs.

(Continued)

*Primary Examiner* — Jonathan Cwern
(74) *Attorney, Agent, or Firm* — Schwegman Lundberg & Woessner, P.A.; Sanjay Agrawal

(57) ABSTRACT

Systems and methods for managing motions of an anatomical region of interest of a patient during image-guided radiotherapy are disclosed. An exemplary system may include an image acquisition device, a radiotherapy device, and a processor device. The processor device may be configured to control the image acquisition device to acquire at least one 2D image. Each 2D image may include a cross-sectional image of the anatomical region of interest. The processor device may also be configured to perform automatic contouring in each 2D image to extract a set of contour elements segmenting the cross-sectional image of the anatomical region of interest in that 2D image. The processor device may be further configured to match the set of contour elements to a 3D surface image of the anatomical (Continued)

region of interest to determine a motion of the anatomical region of interest and to control radiation delivery based on the determined motion.

22 Claims, 6 Drawing Sheets

(51) Int. Cl.
*A61N 5/10* (2006.01)
*G06T 7/38* (2017.01)
*G06T 7/11* (2017.01)

(52) U.S. Cl.
CPC ......... *A61N 5/1049* (2013.01); *A61N 5/1064* (2013.01); *A61N 5/1067* (2013.01); *A61N 5/1068* (2013.01); *G06T 7/0012* (2013.01); *G06T 7/11* (2017.01); *G06T 7/38* (2017.01); *A61N 2005/1055* (2013.01); *G06T 2207/10081* (2013.01); *G06T 2207/10088* (2013.01); *G06T 2207/10104* (2013.01); *G06T 2207/10108* (2013.01); *G06T 2207/20076* (2013.01); *G06T 2207/20116* (2013.01); *G06T 2207/20161* (2013.01); *G06T 2207/30084* (2013.01); *G06T 2207/30096* (2013.01)

(56) References Cited

U.S. PATENT DOCUMENTS

| | | | |
|---|---|---|---|
| 2007/0127845 | A1 | 6/2007 | Fu et al. |
| 2009/0180589 | A1 | 7/2009 | Wang et al. |
| 2009/0326373 | A1 | 12/2009 | Boese et al. |
| 2012/0123251 | A1 | 5/2012 | Erbel et al. |
| 2012/0253178 | A1* | 10/2012 | Mostafavi .............. A61B 5/055 600/413 |
| 2015/0038765 | A1 | 2/2015 | Vilsmeier |
| 2015/0073765 | A1* | 3/2015 | Boettger ................ A61B 5/113 703/11 |
| 2016/0217595 | A1* | 7/2016 | Han ...................... G06T 11/003 |

FOREIGN PATENT DOCUMENTS

| | | |
|---|---|---|
| CN | 101961245 A | 2/2011 |
| CN | 102274039 A | 12/2011 |
| CN | 109069859 | 12/2018 |
| JP | 2008514352 | 5/2008 |
| JP | 2008514352 A | 5/2008 |
| JP | 2009501043 | 1/2009 |
| JP | 2009501043 A | 1/2009 |
| WO | 2017134482 | 8/2017 |

OTHER PUBLICATIONS

"Chinese Application Serial No. 201680084379.6, Office Action dated Oct. 24, 2018", w o English translation, 1 pg.
"International Application Serial No. PCT IB2016 001601, International Preliminary Report on Patentability dated Aug. 16, 2018", 5 pgs.
"International Application Serial No. PCT/IB2016/001601, International Search Report dated Feb. 6, 2017", (Feb. 6, 2017), 3 pgs.
"International Application Serial No. PCT/IB2016/001601, Written Opinion dated Feb. 6, 2017", (Feb. 6, 2017), 3 pgs.
"European Application Serial No. 16889182.8, Extended European Search Report dated Jul. 17, 2019", 11 pgs.
"Japanese Application Serial No. 2018-540393, Notification of Reasons for Refusal dated Jun. 18, 2019", W/ English Translation, 5 pgs.
"Japanese Application Serial No. 2018-540393, Response filed Sep. 5, 2019 to Notification of Reasons for Refusal dated Jun. 18, 2019", w/English claims, 15 pgs.
Furtado, H, et al., "Real-time Intensity Based 2D/3D Registration Using kV-MV Image Pairs for Tumor Motion Tracking in Image Guided Radiotherapy", Progress in Biomedical Optics and Imaging, SPIE—International Society for Optical Engineering, Bellingham, WA, US, vol. 9034, (Mar. 21, 2014), 90340H1-90340H10.
Weese, J, et al., "2D3D Registration and Motion Tracking for Surgical Interventions", Philips Journal of Research, Elsevier, Amsterdam, NL, vol. 51, No. 2., (Jan. 1, 1998), 299-316.
Weese, J, "2D3D Registration and Motion Tracking for Surgical Interventions", Philips Journal of Research, Elsevier, Amsterdam, NL, vol. 51, No. 2., (Jan. 1, 1998), 299-316.
Furtado, H, "Real-time Intensity Based 2D 3D Registration Using kV-MV Image Pairs for Tumor Motion Tracking in Image Guided Radiotherapy", Progress in Biomedical Optics and Imaging, SPIE—International Society for Optical Engineering, Bellingham, WA, US, vol. 9034, (Mar. 21, 2014), 90340H1-90340H10.
"European Application Serial No. 16889182.8, Response filed Apr. 4, 2019 to Office Action dated Sep. 25, 2018", 25 pgs.
"Chinese Application Serial No. 201680084379.6, Office Action dated Dec. 30, 2019", W/English Translation, 24 pgs.
"Chinese Application Serial No. 201680084379.6, Response filed May 13, 2020 to Office Action dated Dec. 30, 2019", w/ English claims, 17 pgs.
"European Application Serial No. 16889182.8, Response filed Feb. 20, 2020 to Extended European Search Report dated Jul. 17, 2019", 29 pgs.
"Chinese Application Serial No. 201680084379.6, Office Action dated Jul. 15, 2020", 16 pgs.
"Chinese Application Serial No. 201680084379.6, Response filed Sep. 16, 2020 to Office Action dated Jul. 15, 2020", w/ English, 17 pgs.
"Chinese Application Serial No. 201680084379.6, Office Action dated Nov. 13, 2020", w/English Translation, 16 pgs.
"Chinese Application Serial No. 201680084379.6, Response filed Dec. 24, 2020 to Office Action dated Nov. 13, 2020", w/ English claims, 31 pgs.

* cited by examiner

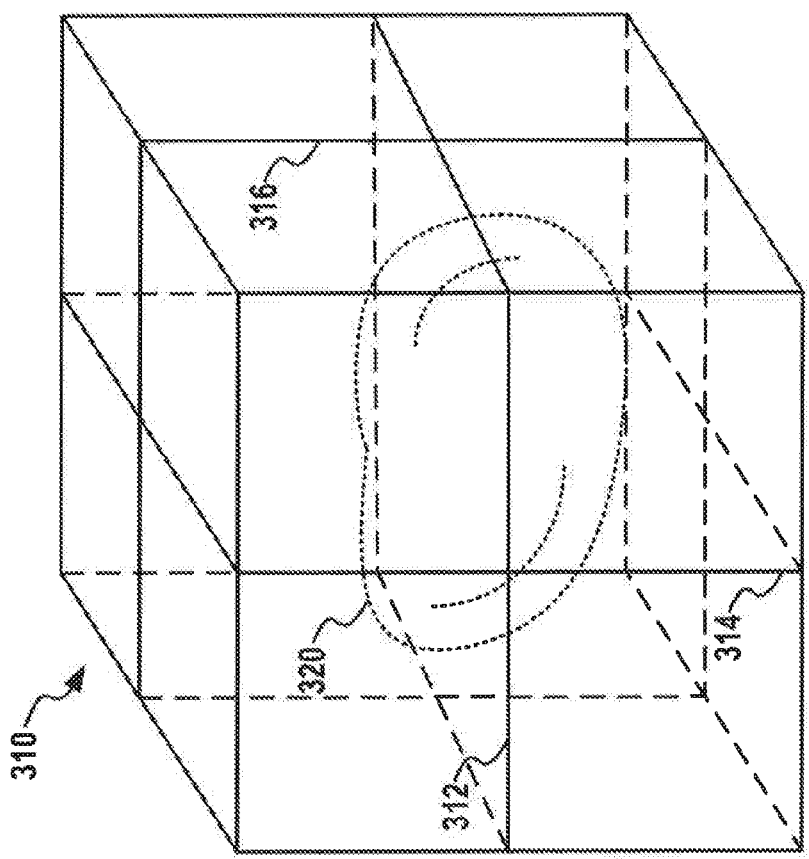

MOTION MANAGEMENT IN IMAGE-GUIDED RADIOTHERAPY USING CONTOUR ELEMENTS

CROSS-REFERENCE TO RELATED APPLICATION

The present application is a U.S. National Stage Filing under 35 U.S.C. 371 from International Application No. PCT/IB2016/001601, filed on Oct. 21, 2016, and published as WO/2017/134482 on Aug. 10, 2017, which claims the benefit of priority to U.S. Provisional Application No. 62/290,198, filed on Feb. 2, 2016; the benefit of priority of each of which is hereby claimed herein, and which applications and publication are hereby incorporated herein by reference in their entirety.

TECHNICAL FIELD

This disclosure relates generally to radiation therapy or radiotherapy. More specifically, this disclosure relates to systems and methods for managing patient motions in image-guided radiotherapy.

BACKGROUND

Radiotherapy is used to treat cancers and other ailments in mammalian (e.g., human and animal) tissue. An exemplary radiotherapy is provided using a linear accelerator (LINAC), whereby a tumor is irradiated by high-energy particles (e.g., electrons, protons, ions and the like). During the course of radiation treatment, images of the tumor and surrounding tissues may be acquired using an image acquisition device to improve the accuracy of radiation field placement. For example, information revealed by the images may be used to compensate for changes of the tumor due to treatment or due to movement of the patient.

Images may be acquired prior to a treatment session to determine changes of the tumor between sessions, or during a treatment session to determine changes of the tumor due to, for example, movements of the patient. Magnetic Resonance Imaging (MRI) techniques may be used to produce such images thanks to its excellent soft tissue contract and high resolution. However, the acquisition time of MRI images, especially three-dimensional (3D) MRI images, is relatively long. For example, a 3D MRI image may take several minutes to acquire. Such a long acquisition time makes 3D MRI unsuitable for tracking movement related tumor changes during a treatment session.

SUMMARY

Certain embodiments of the present disclosure relate to a radiotherapy system. The radiotherapy system may include an image acquisition device configured to acquire images of an anatomical region of interest of a patient. The radiotherapy system may also include a radiotherapy device configured to deliver a dose of radiation to the anatomical region of interest based on the images of the anatomical region of interest. The radiotherapy system may further include a processor device. The processor device may be configured to control the image acquisition device to acquire at least one two-dimensional (2D) image, each of the at least one 2D image including a cross-sectional image of the anatomical region of interest. The processor device may also be configured to perform automatic contouring in each of the at least one 2D image to extract a set of contour elements segmenting the cross-sectional image of the anatomical region of interest in that 2D image. The processor device may also be configured to match the set of contour elements to a three-dimensional (3D) surface image of the anatomical region of interest to determine a motion of the anatomical region of interest. In addition, the processor device may be configured to control radiation delivery based on the determined motion.

Certain embodiments of the present disclosure relate to a method for managing motions of an anatomical region of interest of a patient during an image-guided radiotherapy session. The method may be implemented by a processor device of a radiotherapy system. The method may include controlling an image acquisition device to acquire at least one 2D image. Each of the at least one 2D image may include a cross-sectional image of the anatomical region of interest. The method may also include performing automatic contouring in each of the at least one 2D image to extract a set of contour elements segmenting the cross-sectional image of the anatomical region of interest in that 2D image. The method may also include matching the set of contour elements to a 3D surface image of the anatomical region of interest to determine a motion of the anatomical region of interest. In addition, the method may include controlling a radiotherapy device to deliver radiation based on the determined motion.

Certain embodiments of the present disclosure relate to a radiotherapy system. The radiotherapy system may include an image acquisition device configured to acquire MRI images of an anatomical region of interest of a patient. The radiotherapy system may also include a radiotherapy device including a linear accelerator (LINAC) and configured to deliver a dose of radiation to the anatomical region of interest based on the MRI images of the anatomical region of interest. The radiotherapy system may further include a processor device. The processor device may be configured to control the image acquisition device to acquire a plurality of 2D images. Each of the plurality of 2D images may include a corresponding cross-sectional image of the anatomical region of interest. The plurality of 2D images may include 2D images acquired in at least two of a sagittal plane, a coronal plane, or a transverse plane. The plurality of 2D images may include a first 2D image acquired at a first time point and a second 2D image acquired at a second time point. The second time point may be more recent than the first time point. The first and second 2D images may be acquired at different anatomical planes. The processor device may also be configured to generate a predicted image by advancing the first 2D image forward in time to the second time point based on a periodical motion of the patient. The periodical motion may include a respiratory motion. The processor device may also be configured to perform automatic contouring to extract a first set of contour elements segmenting the cross-sectional image of the anatomical region of interest in the predicted image and a second set contour elements segmenting the cross-sectional image of the anatomical region of interest in the second 2D image. Each of the first and second sets of contour elements may include at least one of a set of points, a set of line segments, or a set of image patches. The processor device may also be configured to match the first and second sets of contour elements to a 3D surface image of the anatomical region of interest by minimizing a distance between the first and second sets of contour elements and the 3D surface to determine a motion of the anatomical region of interest. The motion may include at least one of a displacement or a rotation. In addition, the processor device may be configured to control radiation delivery based on the determined motion, including at least one of controlling a gating of a radiation beam; controlling a modification of a multi-leaf collimator (MLC); or controlling a movement of a patient supporting system.

Additional objects and advantages of the present disclosure will be set forth in part in the following detailed description, and in part will be obvious from the description, or may be learned by practice of the present disclosure. The objects and advantages of the present disclosure will be realized and attained by means of the elements and combinations particularly pointed out in the appended claims.

It is to be understood that the foregoing general description and the following detailed description are exemplary and explanatory only, and are not restrictive of the invention, as claimed.

BRIEF DESCRIPTION OF THE DRAWINGS

The accompanying drawings, which constitute a part of this specification, illustrate several embodiments and, together with the description, serve to explain the disclosed principles.

FIG. 3 illustrates an image of an exemplary anatomical region of interest and exemplary 2D image planes, according to some embodiments of the present disclosure.

DETAILED DESCRIPTION

Figure 1:
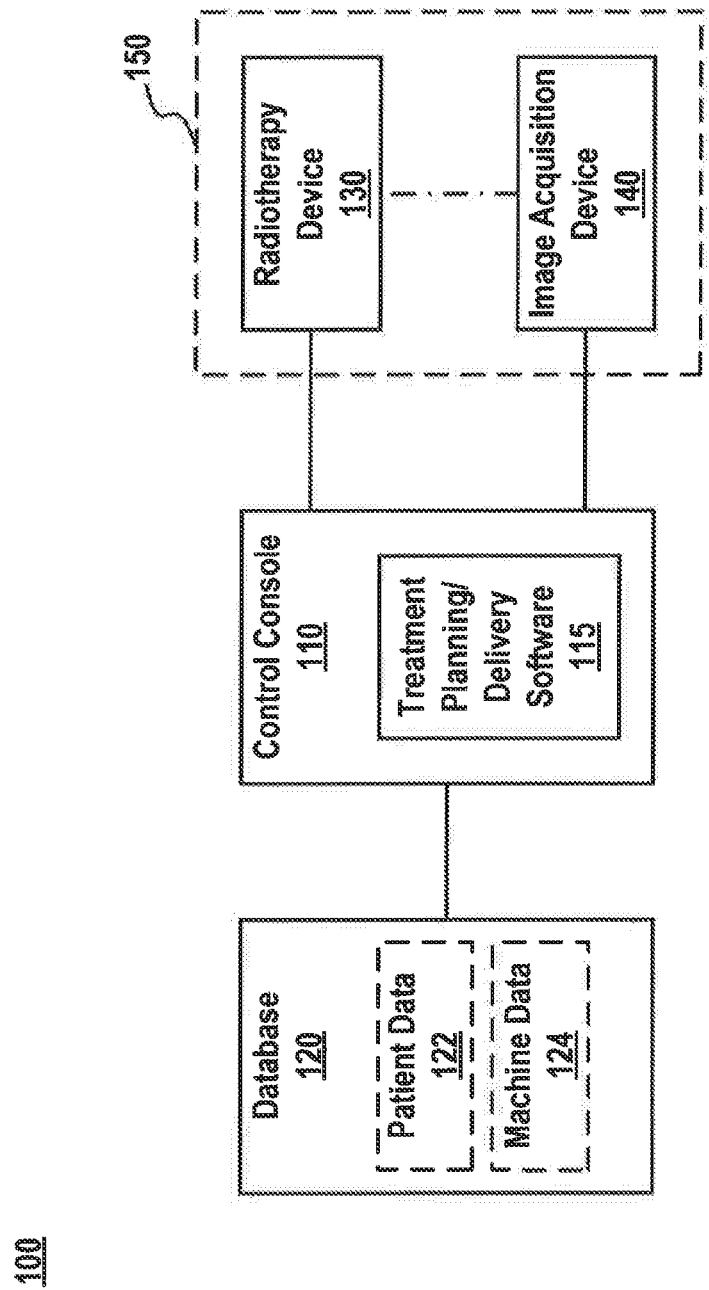
FIG. 1 is a block diagram of an exemplary radiotherapy system, according to some embodiments of the present disclosure.

Exemplary embodiments are described with reference to the accompanying drawings. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be interpreted as open ended, in that, an item or items following any one of these words is not meant to be an exhaustive listing of such item or items, or meant to be limited to only the listed item or items. And the singular forms "a," "an," and "the" are intended to include plural references, unless the context clearly dictates otherwise.

Systems and methods consistent with the present disclosure are directed to image-guided radiation therapy or radiotherapy (IGRT). As used herein, the term "radiation therapy," "radiotherapy," and "radiation oncology" are used interchangeably. IGRT refers to a technique of using frequent 2D or 3D imaging to direct radiotherapy during a course of radiation treatment. IGRT technique may be used to improve the accuracy of radiation field placement, and to reduce the exposure of healthy tissue during radiation treatments.

In IGRT, images may be acquired prior to a treatment session (e.g., prior to applying a radiation dose). For example, in a multi-session treatment, radiation doses may be delivered across several days. Therefore, there may be daily changes in a target subject to radiotherapy. A target may include an organ, a tumor, an anomaly, or an anatomical structure that is subject to or related to radiotherapy. Acquiring an image prior to a treatment session may account for the daily changes in the target. 3D images, such as 3D MRI, CT, and/or ultrasound images may be used as pre-session images.

A target may change not only from day-to-day, but also during a treatment session. For example, the target may move due to movement of the patient such as breathing, coughing, swallowing, etc. Motions during a treatment session may be referred to as intrafractional motions. Because some intrafractional motions occur in a relatively short period of time (e.g., respiratory motions), capturing such motions may require fast imaging techniques. 3D MRI, for example, generally requires 1-5 minutes to acquire an image, and therefore is too slow to track such fast intrafractional motions. Embodiments of the present application enable tracking of fast intrafractional motions using one or more 2D images, which can be acquired much faster than 3D images. For example, a 2D MRI image can be acquired in 50-200 milliseconds. The one or more 2D images may contain cross-sectional images of the target, which can be automatically segmented using auto-contouring techniques. The segmented contour(s) may be matched to a 3D surface image of the target that is acquired prior to the treatment session. Assuming the target is substantially rigid during the treatment session, the matching may generate a motion of the target (e.g., a displacement and/or a rotation) relative to its original position (e.g., the position of the 3D surface in the 3D image acquired prior to the treatment session). In some cases, multiple 2D images acquired in different anatomical planes may be used to provide multiple contours for matching with the 3D surface. For example, images in orthogonal anatomical planes may be used to improve accuracy. In some cases, the multiple 2D images may be acquired at different times (e.g., in sequence), and the time period between successive 2D images may not be insignificant. In these cases, past 2D images acquired earlier in time may be advanced forward in time to generate predicted images approximating images that would have been acquired at a more recent time point. The prediction may be based on the periodic nature of certain patient motions, such as respiratory motions. For example, the cycle of the respiratory motions may be monitored to predict the motion of the target at a particular time point.

FIG. 1 illustrates an exemplary radiotherapy system 100, according to some embodiments of the present disclosure. Radiotherapy system 100 may be an IGRT system. As shown in FIG. 1, radiotherapy system 100 may include a control console 110, a database 120, a radiotherapy device 130, and an image acquisition device 140. In some embodiments, radiotherapy device 130 and image acquisition device 140 may be integrated into a single image-guided radiotherapy device 150, as indicated by the dashed box 150 in FIG. 1. In some embodiments, radiotherapy device 130 and image acquisition device 140 may be separate devices. In some embodiments, radiotherapy device 130 and image acquisition device 140 may be physically or communicative connected to each other, as indicated by a dotted-dashed line between radiotherapy device 130 and image acquisition device 140 in FIG. 1.

Control console 110 may include hardware and software components to control radiotherapy device 130 and image acquisition device 140 and/or to perform functions or operations such as treatment planning, treatment execution, image acquisition, image processing, motion tracking, motion management, or other tasks involved in a radiotherapy process. The hardware components may include one or more computers (e.g., general purpose computers, workstations, servers, terminals, portable/mobile devices, etc.); processor devices (e.g., central processing units (CPUs), graphics processing units (GPUs), microprocessors, digital signal processors (DSPs), field programmable gate arrays (FPGAs), special-purpose or specially-designed processors, etc.); memory/storage devices (e.g., read-only memories (ROMs), random access memories (RAMs), flash memories, hard drives, optical disks, solid-state drives (SSDs), etc.); input devices (e.g., keyboards, mice, touch screens, mics, buttons, knobs, trackballs, levers, handles, joysticks, etc.); output devices (e.g., displays, printers, speakers, vibration devices, etc.); circuitries; printed circuit boards (PCBs); or other suitable hardware. The software components may include operation system software, application software, etc. For example, as shown in FIG. 1, control console 110 may include treatment planning/delivery software 115 that may be stored in a memory/storage device of control console 110. Software 115 may include computer readable and executable codes or instructions. A processor device of control console 110 may be communicatively connected to the memory/storage device storing software 115 to access and execute the codes or instructions. The execution of the codes or instructions may cause the processor device to perform operations to achieve one or more functions consistent with the disclosed embodiments.

Control console 110 may be communicatively connected to database 120 to access data. In some embodiments, database 120 may be implemented using local hardware devices, such as one or more hard drives, optical disks, and/or servers that are in the proximity of control console 110. In some embodiments, database 120 may be implemented in a data center or a server located remotely with respect to control console 110. Control console 110 may access data stored in database 120 through wired or wireless communication.

Database 120 may include patient data 122. Patient data may include information such as imaging data associated with a patient (e.g., MRI, CT, X-ray, PET, SPECT, and the like); anatomical region, organ, or volume of interest segmentation data; functional organ modeling data (e.g., serial versus parallel organs, and appropriate dose response models); radiation dosage data (e.g., may include dose-volume histogram (DVH) information); lab data (e.g., hemoglobin, platelets, cholesterol, triglycerides, creatinine, sodium, glucose, calcium, weight); vital signs (blood pressure, temperature, respiratory rate and the like); genomic data (e.g., genetic profiling); demographics (age, sex, ethnicity, etc.); other diseases affecting the patient (e.g., cardiovascular disease, respiratory disease, diabetes, radiation hypersensitivity syndromes, and the like); medications and drug reactions; diet and lifestyle (e.g., smoking or non-smoking); environmental risk factors; tumor characteristics (histological type, tumor grade, hormone and other receptor status, tumor size, vascularity cell type, cancer staging, Gleason score, etc.); previous treatments (e.g., surgeries, radiation, chemotherapy, hormone therapy, etc.); lymph node and distant metastases status; genetic/protein biomarkers (e.g., MYC, GADD45A, PPMID, BBC3, CDKNIA, PLK3, XPC, AKT1, RELA, BCL2L1, PTEN, CDK1, XIAP, and the like); single nucleotide polymorphisms (SNP) analysis (e.g., XRCC1, XRCC3, APEX1, MDM2, TNFR, MTHFR, MTRR, VEGF, TGFβ, TNFα, etc.), and the like.

Database 120 may include machine data 124. Machine data 124 may information associated with radiotherapy device 130, image acquisition device 140, or other machines relevant to radiotherapy, such as radiation beam size, arc placement, on/off time duration, coordinate system, multi-leaf collimator (MLC) configuration, MRI pulse sequence, and the like.

Image acquisition device 140 may provide medical images of a patient. For example, image acquisition device 140 may provide one or more of MRI images (e.g., 2D MRI, 3D MRI, 2D streaming MRI, 4D volumetric MRI, 4D cine MRI); Computed Tomography (CT) images; Cone-Beam CT images; Positron Emission Tomography (PET) images; functional MRI images (e.g., fMRI, DCE-MRI, diffusion MRI); X-ray images; fluoroscopic images; ultrasound images; radiotherapy portal images; Single-Photo Emission Computed Tomography (SPECT) images; and the like. Accordingly, image acquisition device 140 may include an MRI imaging device, a CT imaging device, a PET imaging device, an ultrasound imaging device, a fluoroscopic device, a SPECT imaging device, or other medical imaging devices for obtaining the medical images of the patient.

Radiotherapy device 130 may include a Leksell Gamma Knife, a LINAC, or other suitable devices capable of delivering radiation to an anatomical region of interest of a patient in a controllable manner.

Figure 2:
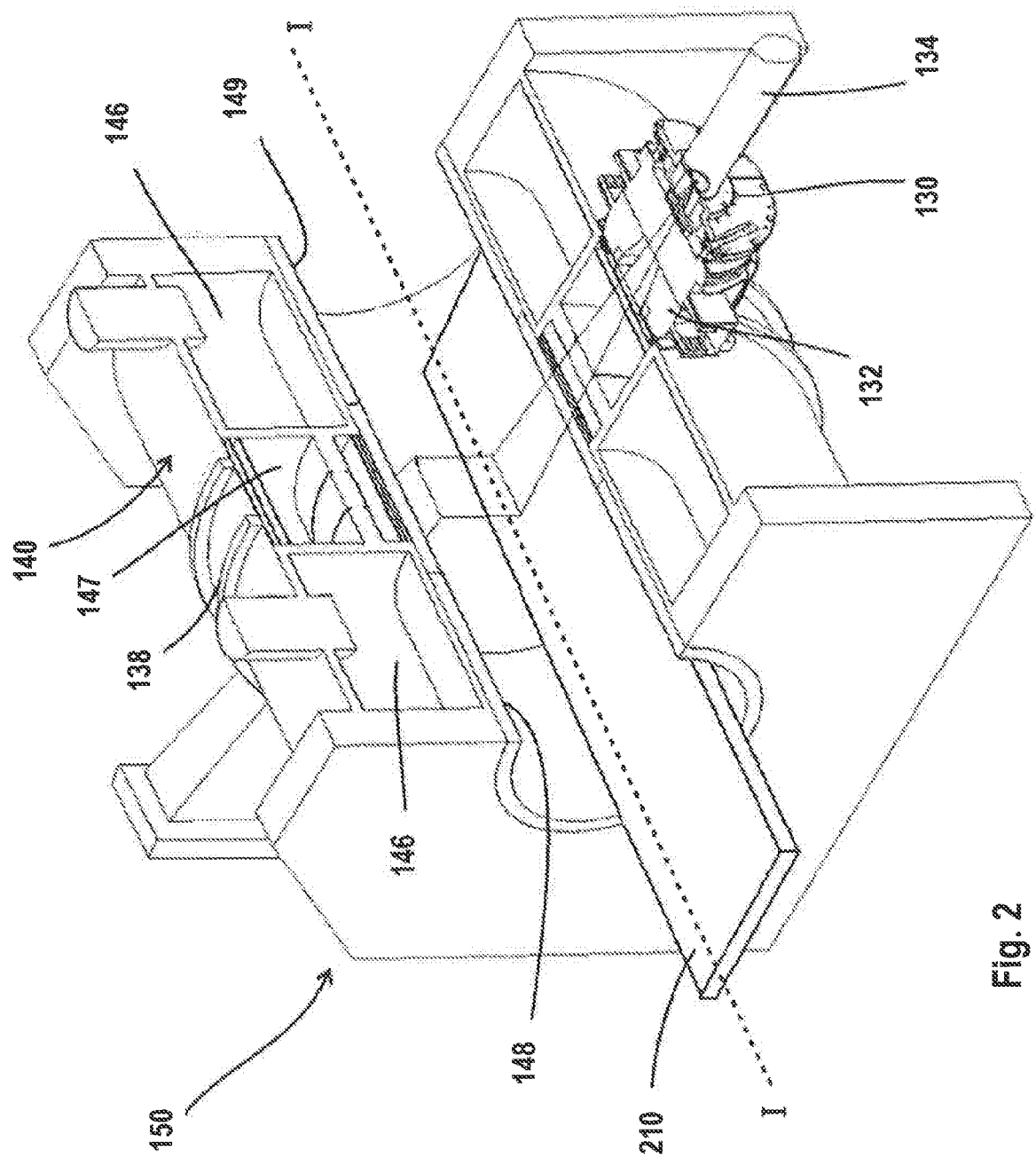
FIG. 2 is a schematic diagram of an exemplary image-guided radiotherapy device, according to some embodiments of the present disclosure.

FIG. 2 illustrates an exemplary image-guided radiotherapy device 150, according to some embodiments of the present disclosure. Device 150 includes a couch 210, an image acquisition portion corresponding to image acquisition device 140, and a radiation delivery portion corresponding to radiotherapy device 130.

Couch 210 may be used for supporting a patient (not shown) during a treatment session, and may also be referred to as a patient supporting system. Couch 210 may be movable along a horizontal, translation axis (labelled "I"), such that the patient resting on couch 210 can be moved into and/or out of device 150. In some embodiments, couch 210 may be rotatable around a central vertical axis of rotation, transverse to the translation axis. Couch 210 may be motorized to move in various directions and rotate along various axes to properly position the patient according to a treatment plan.

Image acquisition device 140 may include an MRI machine used to acquire 2D or 3D MRI images of a patient before, during, and/or after a treatment session. Image acquisition device 140 may include a magnet 146 for generating a primary magnetic field for magnetic resonance imaging. The magnetic field lines generated by operation of magnet 146 may run substantially parallel to the central translation axis I. Magnet 146 may include one or more coils with an axis that runs parallel to the translation axis I. In some embodiments, the one or more coils in magnet 146 may be spaced such that a central window 147 of magnet 146 is free of coils. In other embodiments, the coils in magnet 146 may be thin enough or of a reduced density such that they are substantially transparent to radiation of the wavelength generated by radiotherapy device 130. Image acquisition device 140 may also include one or more active shielding coils, which may generate a magnetic field outside magnet 146 of approximately equal magnitude and opposite polarity to cancel the magnetic field outside magnet 146. A radiation source 134 of radiotherapy device 130 may be positioned in the region where the magnetic field is cancelled, at least to a first order.

Image acquisition device 140 may also include two gradient coils 148 and 149, which may generate a gradient magnetic field that is superposed on the primary magnetic field. Coils 148 and 149 may generate a gradient in the resultant magnetic field that allows spatial encoding of the protons so that their position can be determined. Gradient coils 148 and 149 may be positioned around a common central axis with the magnet 146, and may be displaced from on another along that central axis. The displacement may create a gap, or window, between coils 148 and 149. In the embodiments wherein magnet 146 also includes a central window 147 between coils, the two windows may be aligned with each other.

Radiotherapy device 130 may include the source of radiation 134, such as an X-ray source or a linear accelerator, and a multi-leaf collimator (MLC) 132. Radiotherapy device 130 may be mounted on a chassis 138. Chassis 138 may be continuously rotatable around couch 210 when it is inserted into the treatment area, powered by one or more chassis motors. A radiation detector may also be mounted on chassis 138 if desired, preferably opposite to radiation source 134 and with the rotational axis of chassis 138 positioned between radiation source 134 and the detector. The control circuitry of radiotherapy device 130 may be integrated within device 150 or remote from it, and is functionally represented by control console 110 of FIG. 1.

During a radiotherapy treatment session, a patient may be positioned on couch 210, which may be inserted into the treatment area defined by magnetic coils 146, 148, 149, and chassis 138. Control console 110 may control radiation source 134, MLC 132, and the chassis motor(s) to deliver radiation to the patient through the window between coils 148 and 149.

FIG. 3 illustrates an image of an exemplary anatomical region of interest and exemplary 2D image planes, according to some embodiments of the present disclosure. As used herein, an anatomical region of interest may include an organ, an organ at risk (OAR), a tumor, a surrounding tissue, a radiotherapy target, an isocenter, or any other anatomical structures relevant to radiotherapy. As shown in FIG. 3, a 3D image of an anatomical region of interest 320 may be included in a 3D image 310. For simplicity, the image of anatomical region of interest 320 may also be referred to as anatomical region of interest 320 or target 320. In some embodiment, 3D image 310 may be acquired prior to (e.g., immediately before) application of a radiation dose in a treatment session. For example, 3D image 310 may be a 3D MRI image (or a snapshot of a 4D MRI image), a 3D CT image, a 3D ultrasound image, etc. Once 3D image 310 is acquired, the 3D surface of target 320 may be generated using automatic or manual contouring techniques. The 3D surface may be used to determine intrafractional motions of target 320.

During a radiotherapy session (e.g., radiation beam-on process), one or more 2D images may be acquired to monitor intrafractional motions. Each 2D image may be acquired in an anatomical plane, such as a sagittal plane (e.g., plane 314), a coronal plane (e.g., plane 316), or a transverse plane (e.g., plane 312). As used herein, a sagittal plane is a plane parallel to the sagittal suture, dividing a body into left and right portions; a coronal plane (also known as a frontal plane) divides the body into dorsal and ventral (back and front, or posterior and anterior) portions; a transverse plane divides the body into cranial and caudal (superior and inferior, or head and tail) portions. When multiple 2D images are acquired, the multiple 2D images may be acquired in different anatomical planes (e.g., at least two of the sagittal plane, the coronal plane, and/or the transverse plane). In some embodiments, target 320 may be located at the intersection of the two or more anatomical planes in which the multiple 2D images are acquired. Specific anatomical plane(s) in which 2D image(s) are acquired may be determined by control console 110 based on, for example, the type of the anatomical region of interest, the treatment plan, the medical images of the anatomical region of interest, etc.

Each 2D image may include a cross-sectional image of target 320. Control console 110 may perform automatic contouring in each 2D image to extract a set of contour elements segmenting the cross-sectional image of target 320. Automatic contouring may include image segmentation and may be performed using techniques such as active contour, snakes, level sets, etc. In some embodiment, automatic contouring may be performed immediately following the acquisition of a 2D image. In some embodiments, when multiple 2D images are used, automatic contouring may be performed on certain predicted images undergone time forwarding approximation to advance the acquisition time point forward in time to a more recent time point. In any case, after automatic contouring, a set of contour elements may be extracted from each 2D image segmenting the cross-sectional image of target 320 in that 2D image.

In some embodiments, the set of contour elements may include a set of points. For example, the contour may be represented by a set of image points substantially enclosing or covering at least a portion of the cross-sectional image of target 320. In some embodiments, the set of contour elements may include a set of line segments. For example, the set of line segments may collectively form a substantially continuous curve enclosing at least a portion of the cross-sectional image of target 320. In some embodiments, the set of contour elements may include a set of image patches. For example, the set of image patches may collectively cover at least a portion of the cross-sectional image of target 320.

Figure 4C:
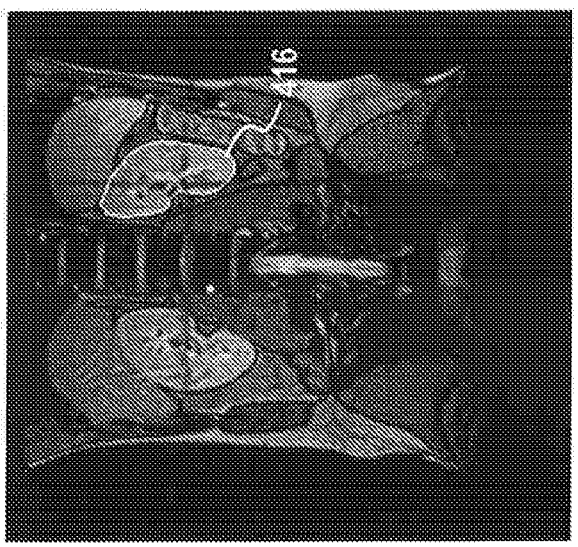
FIGS. 4A-4C illustrate contours of cross-sectional images of an exemplary anatomical region of interest, according to some embodiments of the present disclosure.
Figure 4B:
Figure 4A:
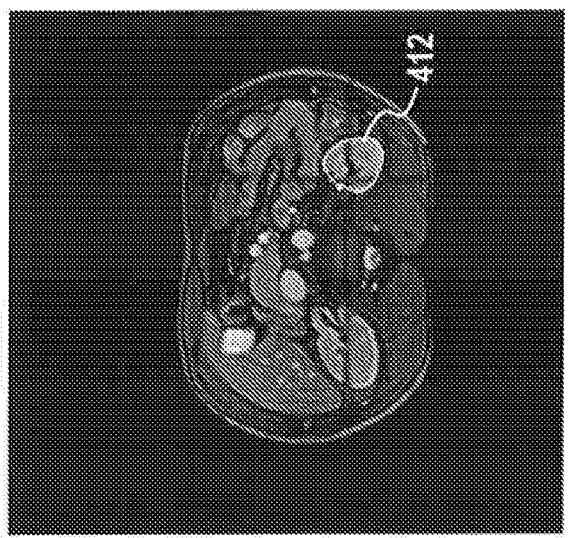

FIGS. 4A-4C are exemplary 2D images showing contours of cross-sectional images of an exemplary anatomical region of interest, according to some embodiments of the present disclosure. Images shown in FIGS. 4A-4C are 2D MRI images of a patient's abdominal area in the transverse plane (4A), the sagittal plane (4B), and the coronal plane (4C). These images include cross-sectional images of an anatomical region of interest—a kidney of a patient, indicated by contours 412, 414, and 416. As described above, contours 412, 414, and 416 may be obtained using automatic contouring techniques.

During a radiotherapy session, the position of an anatomical region of interest, such as the kidney shown in FIGS. 4A-4C, may change. For example, the kidney may move relatively quickly and periodically due to, for example, breathing of the patient. Assuming the kidney is relatively rigid during the radiotherapy session, the moving the kidney may involve displacement and/or rotation. As used herein, a change in the position of an anatomical region of interest such as displacement/rotation is commonly referred to as a motion of the anatomical region of interest. The imaging techniques disclosed herein enable accurate capture of one or more motions of an anatomical region of interest during a radiation delivery session.

Figure 5:
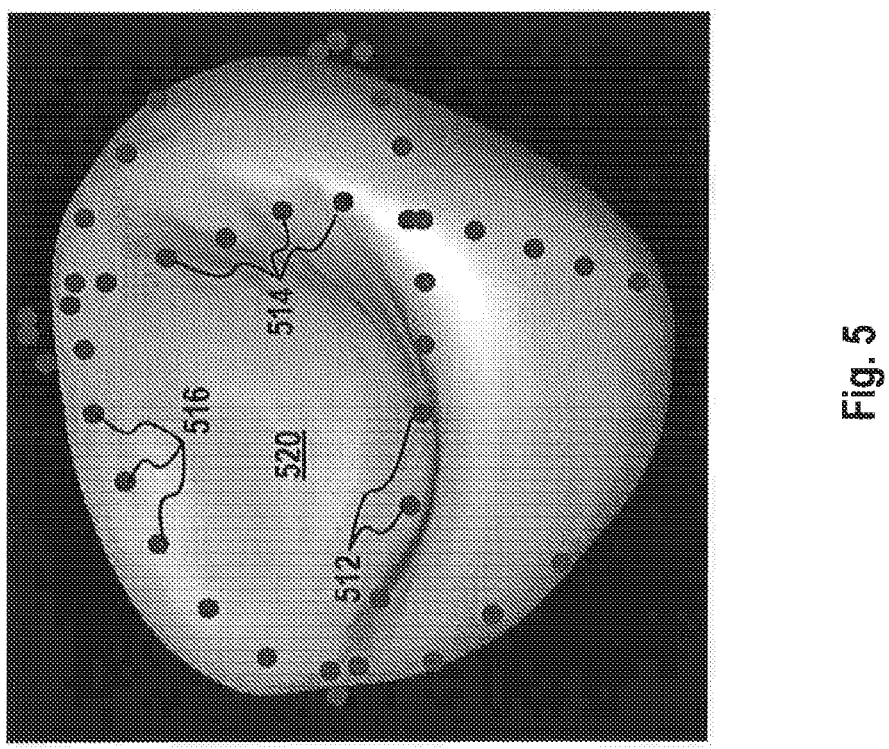
FIG. 5 illustrates an exemplary matching between three exemplary sets of contour elements and an exemplary 3D surface image, according to some embodiments of the present disclosure.

Once one or more contours are extracted, the extracted contour(s) (e.g., the set(s) of contour elements) may be used to determine a motion of target 320 by matching the contour(s) to the 3D surface image of target 320 acquired prior to the treatment session. FIG. 5 illustrates an exemplary matching between three exemplary sets of contour elements and an exemplary 3D surface image 520. As shown in FIG. 5, 3D surface image 520 may be obtained from a 3D image acquired prior to the treatment session using automatic or manual contouring techniques. Three sets of contour elements 512, 514, and 516 may be extracted from three 2D images acquired in the transverse plane, the sagittal plane, and the coronal plane, respectively, using automatic contouring techniques, as described above. In FIG. 5, the three sets of contour elements are image points. In other embodiment, line segments or image patches may also be used. When no motion occurs (e.g. neither displacement nor rotation occurs) between the acquisition of the 3D image from which 3D surface image 520 is extracted and the acquisition of each of the 2D images from which the set contour elements 512, 514, or 516 is extract, the three sets of contour elements 512, 514, and 516 should substantially match the 3D surface image 520. If, however, certain motion occurs, such as when displacement and/or rotation occurs, mismatch between the three sets of contour elements 512, 514, and 516 and the 3D surface image 520 may also occur. Because the anatomical region of interest is assumed to be relatively rigid, optimizing the matching between the three sets of contour elements 512, 514, and 516 and the 3D surface image 520 may result in displacement and/or rotation of the 3D surface image 520 that substantially track the motion of the anatomical region of interest that actually occurs. Therefore, control console 110 may determine the motion of the anatomical region of interest by matching the set(s) of contour elements (e.g., 512, 514, 516) to the 3D surface image (e.g., 520). For example, the matching may be performed using an iterative closest point (ICP) algorithm that minimizes a distance between the contour elements and the 3D surface. The distance may be calculated as a summation of individual distances between each contour element and the 3D surface. For example, in FIG. 5, an individual distance between a point and the surface may be calculated as the shortest distance between the point and the surface. The distance between all three sets of points and the surface may be the summation of all individual distances. The matching algorithm may then seek to minimize the distance by displacing and/or rotating 3D surface 520, and use the resulting displacement and/or rotation as an approximation of the actual motion of the anatomical region of interest.

Figure 6:
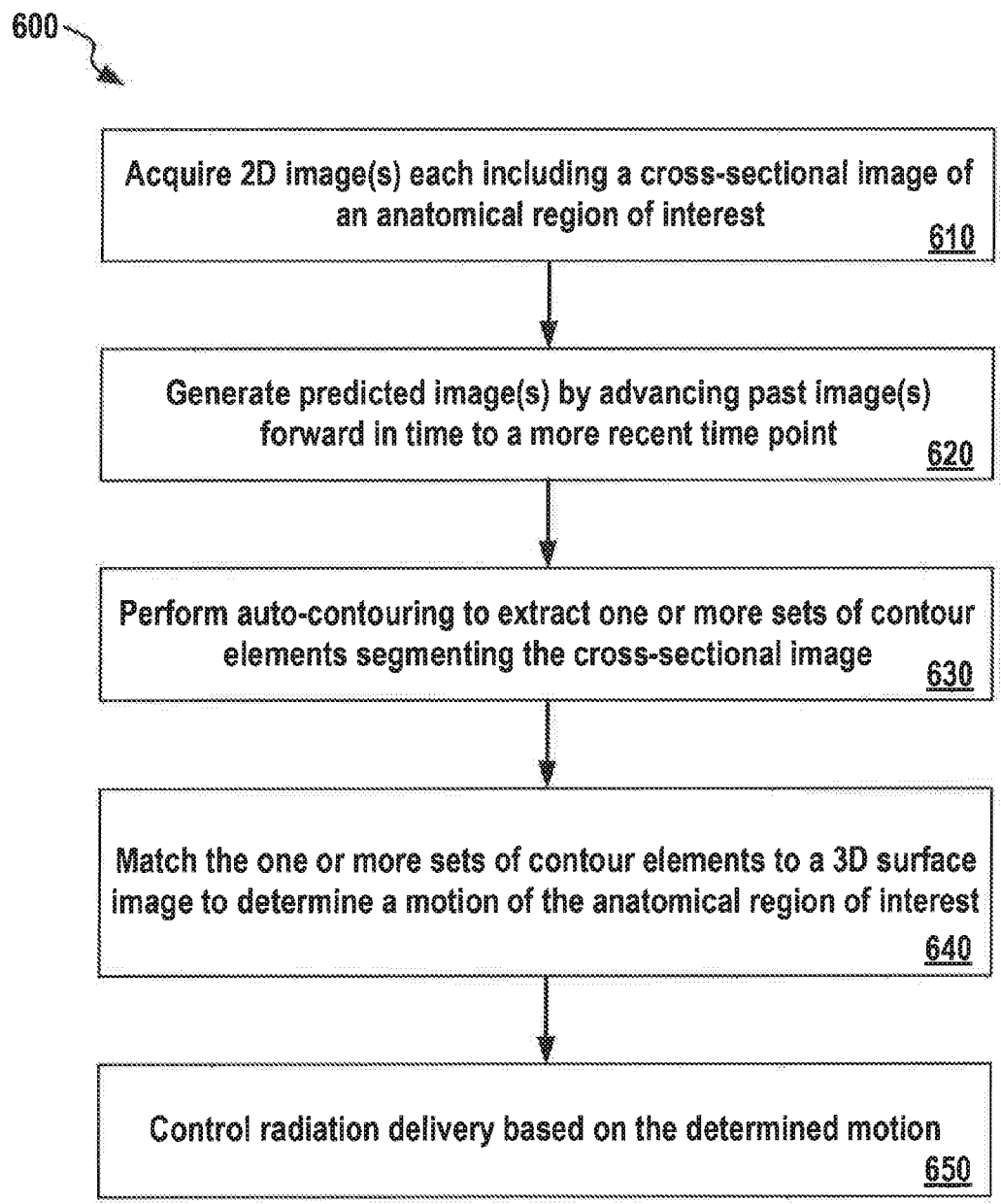
FIG. 6 is a flowchart of an exemplary method of managing motions of an anatomical region of interest of a patient during an image-guided radiotherapy session, according to some embodiments of the present disclosure.

FIG. 6 is a flowchart of an exemplary method 600 of managing motions of an anatomical region of interest of a patient during an image-guided radiotherapy session, according to some embodiments of the present disclosure. Method 600 includes a plurality of steps, some of which may be optional.

In step 610, control console 110 may control image acquisition device 140 to acquire at least one 2D image (e.g., FIGS. 4A-4C). Each acquired 2D image may include a cross-sectional image of an anatomical region of interest (e.g., cross-sectional images indicated by contours 412, 414, and 416).

In step 620, control console 110 may generate one or more predicted images by advancing any past image(s) forward in time to a more recent time point.

In some embodiments, multiple 2D images may be acquired at different time points. For example, images shown in FIGS. 4A-4C may be acquired at $t_1$, $t_2$, and $t_3$, respectively, where $t_1<t_2<t_3$. In other words, the image shown in FIG. 4C is the most recent image. While images shown in FIGS. 4A-4C may be acquired sequentially, the time delay between successive images may not be insignificant in some cases. Therefore, images acquired at an earlier time point may be advanced forward in time to a more recent time point. For example, the image shown in FIG. 4A may be advanced forward in time (e.g., $t_1$->$t_3$) such that a predicted image may be generated to approximate a "would-be" image as if FIG. 4A is acquired at $t_3$. Similarly, the image shown in FIG. 4B may be advance forward in time from $t_2$ to $t_3$. Once FIGS. 4A and 4B are brought to the same time point as FIG. 4C, automatic contouring may be performed to extract the corresponding set of contour elements in each figure. These sets of contour elements, assuming being extracted from images acquired at the same time point, can be used to match to the 3D surface image (e.g., 520) to determine the motion of the anatomical region of interest. In some embodiments, automatic contouring may be performed on original 2D images to extract a set of contour elements. The set of contour elements may then be modified to account for the time-forwarding effect.

In some embodiments, control console 110 may generate the predicted image undergone time forwarding based on a periodical motion of the patient. For example, when the motion of the anatomical region of interest is primary due to a periodical motion of the patient, such as a respiratory motion, the pattern of the periodical motion may be monitored and analyzed. For example, multiple cycles of the periodical motion may be recorded to generate a prediction model for predicting the motion of the anatomical region of interest. In some embodiment, the prediction may be reflected by an approximate change in position of certain cross-sectional image portions in a 2D image. Statistical method may be used to improve the accuracy of the prediction. In some embodiments, the prediction model may predict the position of a cross-sectional portion in a 2D image (e.g., the cross-sectional image of the anatomical region of interest) and modify the contour(s) extracted from original 2D images based on the prediction.

In step 630, control console 110 may perform automatic contouring in each 2D image (e.g., FIGS. 4A-4C) to extract a set of contour elements (e.g., 412, 414, and 416) segmenting the cross-sectional image in that 2D image. As described above, the automatic contouring may be performed using a segmentation algorithm such as active contour, snakes, level sets, etc. The set of contour elements may include points, line segments, and/or image patches.

In step 640, control console 110 may match one or more sets of contour elements to a 3D surface image (e.g., 520) to determine a motion of the anatomical region of interest. For example, the matching may be performed using a surface match algorithm such as ICP algorithm, which minimizes the distance between the contour elements and the 3D surface. As described above, the motion of the anatomical region of interest may include displacement and/or rotation.

Once a motion is detected, control console 110 may control radiation delivery, including performing various operations, to compensate for the motion. For example, in step 650, control console 110 may control radiotherapy device 130 to gate a radiation beam if a certain motion exceeds a threshold. In another example, control console 110 may modify the configuration of a MLC (e.g., MLC 132) to change the beam shape. In another example, control console 110 may move patient support system 210 and/or chassis motor(s) to realign the anatomical region of interest with the isocenter of the radiation beams. Other operation or treatment parameters may also be changed based on the determined motion.

Various operations or functions are described herein, which may be implemented or defined as software code or instructions. Such content may be directly executable ("object" or "executable" form), source code, or difference code ("delta" or "patch" code). Software implementations of the embodiments described herein may be provided via an article of manufacture with the code or instructions stored thereon, or via a method of operating a communication interface to send data via the communication interface. A machine or computer readable storage medium may cause a machine to perform the functions or operations described, and includes any mechanism that stores information in a form accessible by a machine (e.g., computing device, electronic system, and the like), such as recordable/non-recordable media (e.g., read only memory (ROM), random access memory (RAM), magnetic disk storage media, optical storage media, flash memory devices, and the like). A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present invention also relates to a system for performing the operations herein. This system may be specially constructed for the required purposes, or it may comprise a general-purpose computer selectively activated or reconfigured by a computer program stored in the computer. Such a computer program may be stored in a computer readable storage medium, such as, but not limited to, any type of disk including floppy disks, optical disks, CDROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

Embodiments of the invention may be implemented with computer-executable instructions. The computer-executable instructions may be organized into one or more computer-executable components or modules. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described herein.

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements.

Having described aspects of the invention in detail, it will be apparent that modifications and variations are possible without departing from the scope of aspects of the invention as defined in the appended claims. As various changes could be made in the above constructions, products, and methods without departing from the scope of aspects of the invention, it is intended that all matter contained in the above description and shown in the accompanying drawings shall be interpreted as illustrative and not in a limiting sense.

What is claimed is:

1. A radiotherapy system, comprising:
an image acquisition device configured to acquire images of an anatomical region of interest of a patient;
a radiotherapy device configured to deliver a dose of radiation to the anatomical region of interest based on the images of the anatomical region of interest; and
a processor device configured to:
control the image acquisition device to acquire:
a three-dimensional (3D) image of the anatomical region of interest of the patient; and
a first two-dimensional (2D) image corresponding to a first plane at a first time point and a second 2D image corresponding to a second plane at a second time point, the second time point being more recent than the first time point, the first time point and the second time point corresponding to a same phase in a periodical motion of the patient, each of the first and second 2D images including a cross-sectional image of the anatomical region of interest of the patient;
modify a first contour element of the first 2D image, corresponding to the first plane at the first time point, based on the periodical motion of the patient to represent the first contour element of the first 2D image at the second time point;
obtain a 3D surface image from the 3D image of the anatomical region of interest of the patient;
match, to the 3D surface image obtained from the 3D image of the anatomical region of interest of the patient, the first contour element of the first 2D image corresponding to the first plane that has been modified based on the periodical motion of the patient and an original second contour element of the second 2D image corresponding to the second plane to determine motion of the anatomical region of interest; and
control radiation delivery based on the determined motion.

2. The radiotherapy system of claim 1, wherein the image acquisition device is configured to acquire 2D Magnetic Resonance Imaging (MRI) images of the anatomical region of interest of the patient.

3. The radiotherapy system of claim 1, wherein the modified first contour element depicts an approximation of the anatomical region of interest at the second time point, wherein the radiotherapy device includes a linear accelerator (LINAC).

4. The radiotherapy system of claim 1, wherein the processor is further configured to synchronize contour elements of the first and second 2D images to a common time point prior to matching the contour elements of the first and second 2D images to the 3D surface image, the common time point being different from the first and second time points at which the first and second 2D images were acquired, wherein the first or second contour elements includes at least one of:
  a set of points;
  a set of line segments; or
  a set of image patches.

5. The radiotherapy system of claim 1, wherein the first and second 2D images include 2D images acquired in at least two of a sagittal plane, a coronal plane, or a transverse plane.

6. The radiotherapy system of claim 1, wherein the processor is further configured to modify the first contour element by:
  extracting the first contour element from the first 2D image;
  applying a prediction model to predict a change in a position of a cross-sectional portion of the first 2D image; and
  modifying the extracted first contour element based on the predicted change in the position.

7. The radiotherapy system of claim 1, wherein the periodical motion of the patient includes a respiratory motion, and wherein the processor is further configured to:
  control the image acquisition device to acquire a third two-dimensional (2D) image corresponding to a third plane at a third time point that is more recent than the second point in time;
  modify the second contour element of the second 2D image, corresponding to the second plane at the second time point, based on the periodical motion of the patient, wherein the modified first contour element, the modified second contour element and a third contour element of the third 2D image correspond to a common time point comprising the third time point; and
  match the modified first contour element of the first 2D image corresponding to the first plane, the modified second contour element of the second 2D image corresponding to the second plane, and the third contour element of the third 2D image corresponding to the third plane to the 3D surface image to determine the motion of the anatomical region of interest.

8. The radiotherapy system of claim 1, wherein the processor device is configured to:
  match the first and second contour elements to the 3D surface image of the anatomical region of interest by minimizing a distance between the first and second contour elements and the 3D surface.

9. The radiotherapy system of claim 1, wherein the motion of the anatomical region of interest includes at least one of a displacement or a rotation.

10. The radiotherapy system of claim 1, wherein the processor device is configured to determine the motion and control the radiation delivery during a radiotherapy session.

11. The radiotherapy system of claim 1, wherein the processor device is configured to control at least one of the following based on the determined motion:
  a gating of a radiation beam;
  a modification of a multi-leaf collimator (MLC); or
  a movement of a patient supporting system.

12. A method for managing motions of an anatomical region of interest of a patient during an image-guided radiotherapy session, implemented by a processor device of a radiotherapy system, the method comprising:
  controlling an image acquisition device to acquire:
    a three-dimensional (3D) image of the anatomical region of interest of the patient; and
    a first two-dimensional (2D) image corresponding to a first plane at a first time point and a second 2D image corresponding to a second plane at a second time point, the second time point being more recent than the first time point, the first time point and the second time point corresponding to a same phase in a periodical motion of the patient, each of the first and second 2D images including a cross-sectional image of the anatomical region of interest of the patient;
  modifying a first contour element of the first 2D image, corresponding to the first plane at the first time point, based on the periodical motion of the patient to represent the first contour element of the first 2D image at the second time point;
  obtaining a 3D surface image from the 3D image of the anatomical region of interest of the patient;
  matching, to the 3D surface image obtained from the 3D image of the anatomical region of interest of the patient, the first contour element of the first 2D image corresponding to the first plane that has been modified based on the periodical motion of the patient and an original second contour element of the second 2D image corresponding to the second plane to determine motion of the anatomical region of interest; and
  controlling a radiotherapy device to deliver radiation based on the determined motion.

13. The method of claim 12, and wherein the image acquisition device is configured to acquire 2D Magnetic Resonance Imaging (MRI) images of the anatomical region of interest of the patient.

14. The method of claim 12, wherein the radiotherapy device includes a linear accelerator (LINAC).

15. The method of claim 12, wherein the first and second contour elements include at least one of:
  a set of points;
  a set of line segments; or
  a set of image patches.

16. The method of claim 12, wherein the first and second 2D images include 2D images acquired in at least two of a sagittal plane, a coronal plane, or a transverse plane.

17. The method of claim 12, further comprising:
  extracting the first contour element from the first 2D image;
  applying a prediction model to predict a change in a position of a cross-sectional portion of the first 2D image; and
  adjusting the extracted first contour element based on the predicted change in the position.

18. The method of claim 12, wherein the periodical motion of the patient includes a respiratory motion, further comprising:
  controlling the image acquisition device to acquire a third two-dimensional (2D) image corresponding to a third plane at a third time point that is more recent than the second point in time;
  modifying the second contour element of the second 2D image, corresponding to the second plane at the second time point, based on the periodical motion of the patient, wherein the modified first contour element, the modified second contour element and a third contour element of the third 2D image correspond to a common time point comprising the third time point; and
  matching the modified first contour element of the first 2D image corresponding to the first plane, the modified second contour element of the second 2D image corresponding to the second plane, and the third contour element of the third 2D image corresponding to the third plane to the 3D surface image to determine the motion of the anatomical region of interest.

19. The method of claim 12, comprising:
matching the first and second contour elements to the 3D surface image of the anatomical region of interest by minimizing a distance between the first and second contour elements and the 3D surface.

20. The method of claim 12, wherein the radiotherapy device is controlled during a radiotherapy session.

21. The method of claim 12, wherein controlling the radiotherapy device to deliver radiation based on the determined motion includes at least one of:
controlling a gating of a radiation beam;
controlling a modification of a multi-leaf collimator (MLC); or
controlling a movement of a patient supporting system.

22. A radiotherapy system, comprising:
an image acquisition device configured to acquire Magnetic Resonance Imaging (MRI) images of an anatomical region of interest of a patient;
a radiotherapy device including a linear accelerator (LINAC) and configured to deliver a dose of radiation to the anatomical region of interest based on the MRI images of the anatomical region of interest; and
a processor device configured to:
control the image acquisition device to acquire a three-dimensional (3D) image of the anatomical region of interest of the patient and a plurality of 2D images, each of the plurality of 2D images including a corresponding cross-sectional image of the anatomical region of interest, wherein the plurality of 2D images include 2D images acquired in at least two of a sagittal plane, a coronal plane, or a transverse plane, and wherein the plurality of 2D images include a first 2D image acquired at a first time point and a second 2D image acquired at a second time point, the second time point being more recent than the first time point, and wherein the first and second 2D images are acquired at different anatomical planes;
modify a first contour element of a first 2D image of the plurality of 2D images, corresponding to a first plane of the anatomical planes at the first time point, based on periodical motion of the patient to represent the first contour element of the first 2D image at the second time point;
obtain a 3D surface image from the 3D image of the anatomical region of interest of the patient;
match, to the 3D surface image obtained from the 3D image of the anatomical region of interest of the patient, the first contour element of the first 2D image corresponding to the first plane that has been modified based on the periodical motion of the patient and an original second contour element of a second 2D image of the plurality of 2D images corresponding to a second plane of the anatomical planes by minimizing a distance between the first and second contour elements and the 3D surface image to determine motion of the anatomical region of interest, the motion including at least one of a displacement or a rotation; and
control radiation delivery based on the determined motion during a radiotherapy session, including at least one of:
controlling a gating of a radiation beam;
controlling a modification of a multi-leaf collimator (MLC); or
controlling a movement of a patient supporting system.

* * * * *